(12) United States Patent
Alon

(10) Patent No.: US 9,452,261 B2
(45) Date of Patent: Sep. 27, 2016

(54) LOW VOLUME ACCURATE INJECTOR

(75) Inventor: Ruth Alon, Michmoret (IL)

(73) Assignee: MEDIMOP MEDICAL PROJECTS LTD., Ra'Anana (IL)

(*) Notice: Subject to any disclaimer, the term of this patent is extended or adjusted under 35 U.S.C. 154(b) by 251 days.

(21) Appl. No.: 13/643,470

(22) PCT Filed: May 8, 2011

(86) PCT No.: PCT/IL2011/000368
§ 371 (c)(1),
(2), (4) Date: Oct. 25, 2012

(87) PCT Pub. No.: WO2011/141907
PCT Pub. Date: Nov. 17, 2011

(65) Prior Publication Data
US 2013/0041346 A1    Feb. 14, 2013

Related U.S. Application Data

(60) Provisional application No. 61/332,855, filed on May 10, 2010.

(51) Int. Cl.
*A61M 5/20* (2006.01)
*A61M 5/142* (2006.01)
(Continued)

(52) U.S. Cl.
CPC .............. *A61M 5/20* (2013.01); *A61M 5/1452* (2013.01); *A61M 5/14244* (2013.01); *A61M 5/24* (2013.01);
(Continued)

(58) Field of Classification Search
CPC ............. A61M 5/20; A61M 5/14244; A61M 5/1452; A61M 5/24; A61M 5/3146; A61M 5/3156; A61M 5/3202; A61M 5/484; A61M 5/488; A61M 5/31575; A61M 2005/31588; A61M 2005/2414; A61M 2005/3125; A61M 2005/312

USPC ................... 604/93.01, 117, 118, 121–122, 604/124–125, 131, 156, 181, 187, 200–201, 604/207–212, 214, 217–218, 232, 244, 246, 604/264, 272, 506

See application file for complete search history.

(56) References Cited

U.S. PATENT DOCUMENTS 1,795,630 A    3/1931  Wilson
2,860,635 A    11/1958 Wilburn
(Continued)

FOREIGN PATENT DOCUMENTS

CN    1747683 A    3/2006
CN    1863566 A    11/2006
(Continued)

OTHER PUBLICATIONS

Daikyo Crystal Zenith® polymer, Manufactured by Daikyo Seiko, Ltd.
(Continued)

*Primary Examiner* — Kevin C Sirmons
*Assistant Examiner* — Amber Stiles
(74) *Attorney, Agent, or Firm* — Panitch Schwarze Belisario & Nadel LLP

(57) ABSTRACT

Substance-administration apparatus (20) is provided, including a housing (22), and a needle (80), couplable to the housing (22), having a skin-insertion portion 0.3-2.5 mm in length and an outer diameter less than 0.23 mm. A dosage regulator (60) regulates a dosage of substance injected in a single injection through the needle (80). Dosage is selectable by a setting of the dosage regulator (60) as one of a plurality of selectable dosages. At least one dosage is less than or equal to 10 ul. An injection driver (54), activatable by a user, drives the substance through the needle (80). A motor coupled to the injection driver (54) is actuated by the dosage regulator (60) in a pulsatile manner to produce brief periods of high pressure in the apparatus (20) that expel a predetermined volume of the substance through the needle (80) at a controlled rate. Other applications are also described.

28 Claims, 7 Drawing Sheets

Figure 11:
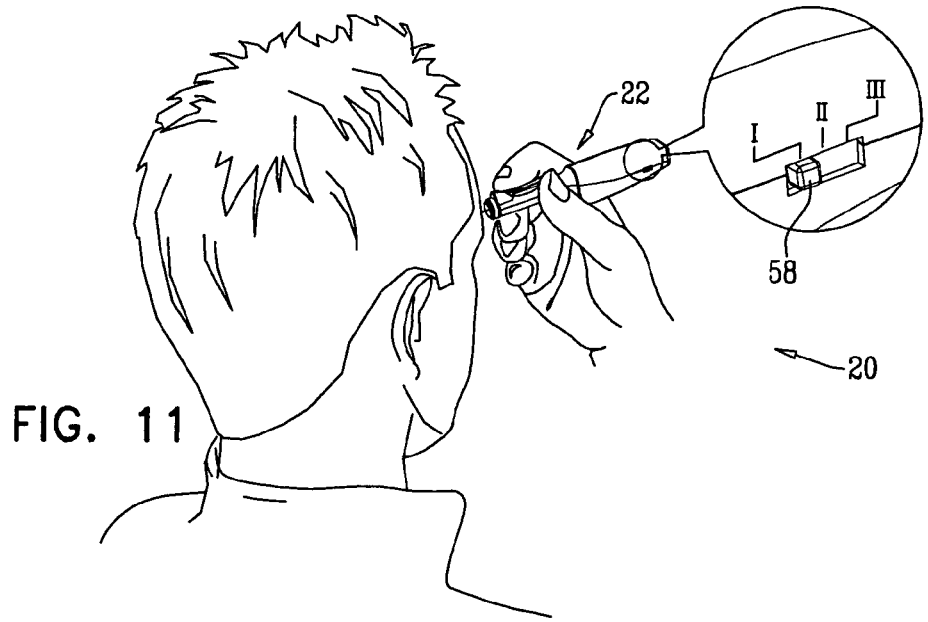

(51) Int. Cl.
  *A61M 5/145* (2006.01)
  *A61M 5/24* (2006.01)
  *A61M 5/31* (2006.01)
  *A61M 5/315* (2006.01)
  *A61M 5/32* (2006.01)
  *A61M 5/48* (2006.01)

(52) U.S. Cl.
  CPC .......... *A61M 5/3146* (2013.01); *A61M 5/3156* (2013.01); *A61M 5/31575* (2013.01); *A61M 5/3202* (2013.01); *A61M 5/484* (2013.01); *A61M 5/488* (2013.01); *A61M 2005/2411* (2013.01); *A61M 2005/3125* (2013.01); *A61M 2005/3126* (2013.01); *A61M 2005/31588* (2013.01)

(56) References Cited

U.S. PATENT DOCUMENTS

| | | |
|---|---|---|
| 3,203,269 A | 8/1965 | Perrine |
| 3,212,685 A | 10/1965 | Swan et al. |
| 3,794,028 A * | 2/1974 | Mueller ............... A61M 5/00 604/506 |
| 3,994,295 A | 11/1976 | Wulff |
| 4,195,636 A | 4/1980 | Behnke |
| 4,218,724 A | 8/1980 | Kaufman |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,685,903 A | 8/1987 | Cable et al. |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,919,596 A | 4/1990 | Slate et al. |
| 4,929,241 A | 5/1990 | Kulli |
| 4,950,246 A | 8/1990 | Muller |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,662,678 A | 9/1997 | Macklin |
| 5,672,160 A | 9/1997 | Osterlind et al. |
| 5,690,618 A * | 11/1997 | Smith ................ A61M 5/20 128/DIG. 1 |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,589,229 B1 | 7/2003 | Connelly et al. |
| 6,595,956 B1 * | 7/2003 | Gross ................ A61M 5/14248 128/DIG. 12 |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |

(56) References Cited

U.S. PATENT DOCUMENTS

| | | |
|---|---|---|
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |

(56) References Cited

U.S. PATENT DOCUMENTS

| | | | |
|---|---|---|---|
| 8,790,295 | B1 | 7/2014 | Sigg et al. |
| 8,795,224 | B2 | 8/2014 | Starkweather et al. |
| 8,795,231 | B2 | 8/2014 | Chong et al. |
| 8,795,260 | B2 | 8/2014 | Drew |
| 8,801,668 | B2 | 8/2014 | Ali et al. |
| 8,801,679 | B2 | 8/2014 | Iio et al. |
| 8,810,394 | B2 | 8/2014 | Kalpin |
| 8,814,379 | B2 | 8/2014 | Griffiths et al. |
| 9,061,104 | B2 | 6/2015 | Daniel |
| 9,061,110 | B2 | 6/2015 | Avery et al. |
| 9,089,475 | B2 | 7/2015 | Fangrow |
| 9,089,641 | B2 | 7/2015 | Kavazov |
| 2001/0025168 | A1 | 9/2001 | Gross et al. |
| 2001/0041869 | A1 | 11/2001 | Causey et al. |
| 2002/0010423 | A1 | 1/2002 | Gross et al. |
| 2002/0029018 | A1 | 3/2002 | Jeffrey |
| 2002/0040208 | A1 | 4/2002 | Flaherty et al. |
| 2002/0055711 | A1 | 5/2002 | Lavi et al. |
| 2002/0065488 | A1 | 5/2002 | Suzuki et al. |
| 2002/0107487 | A1 | 8/2002 | Preuthun |
| 2002/0123740 | A1 | 9/2002 | Flaherty et al. |
| 2002/0161332 | A1 | 10/2002 | Ramey |
| 2002/0169215 | A1 | 11/2002 | Meng |
| 2003/0009133 | A1 | 1/2003 | Ramey |
| 2003/0125671 | A1* | 7/2003 | Aramata et al. ............... 604/236 |
| 2003/0135159 | A1 | 7/2003 | Daily et al. |
| 2003/0160683 | A1 | 8/2003 | Blomquist |
| 2003/0171717 | A1 | 9/2003 | Farrugia et al. |
| 2004/0010207 | A1 | 1/2004 | Flaherty et al. |
| 2004/0092873 | A1 | 5/2004 | Moberg |
| 2004/0116866 | A1 | 6/2004 | Gorman et al. |
| 2004/0127857 | A1 | 7/2004 | Shemesh et al. |
| 2004/0158172 | A1 | 8/2004 | Hancock |
| 2004/0186419 | A1 | 9/2004 | Cho |
| 2004/0260233 | A1 | 12/2004 | Garibotto et al. |
| 2005/0033234 | A1 | 2/2005 | Sadowski et al. |
| 2005/0065466 | A1 | 3/2005 | Vedrine |
| 2005/0065472 | A1 | 3/2005 | Cindrich et al. |
| 2005/0071487 | A1 | 3/2005 | Lu et al. |
| 2005/0113761 | A1 | 5/2005 | Faust et al. |
| 2005/0159706 | A1 | 7/2005 | Wilkinson et al. |
| 2005/0171476 | A1* | 8/2005 | Judson ............... A61M 5/14566 604/131 |
| 2005/0171512 | A1 | 8/2005 | Flaherty |
| 2005/0177136 | A1 | 8/2005 | Miller |
| 2005/0197650 | A1 | 9/2005 | Sugimoto et al. |
| 2005/0203461 | A1 | 9/2005 | Flaherty et al. |
| 2005/0238507 | A1 | 10/2005 | Dilanni et al. |
| 2005/0283114 | A1 | 12/2005 | Bresina et al. |
| 2006/0013716 | A1* | 1/2006 | Nason ............... A61M 5/14244 417/437 |
| 2006/0030816 | A1* | 2/2006 | Zubry ............... A61M 5/24 604/131 |
| 2006/0095014 | A1 | 5/2006 | Ethelfeld |
| 2006/0122577 | A1 | 6/2006 | Poulsen et al. |
| 2006/0173406 | A1 | 8/2006 | Hayes et al. |
| 2006/0173439 | A1 | 8/2006 | Thorne et al. |
| 2006/0195029 | A1 | 8/2006 | Shults et al. |
| 2006/0211982 | A1 | 9/2006 | Prestrelski et al. |
| 2006/0229569 | A1 | 10/2006 | Lavi et al. |
| 2006/0264889 | A1 | 11/2006 | Moberg et al. |
| 2006/0264890 | A1 | 11/2006 | Moberg et al. |
| 2006/0264894 | A1 | 11/2006 | Moberg et al. |
| 2006/0270987 | A1 | 11/2006 | Peter |
| 2006/0283465 | A1 | 12/2006 | Nickel et al. |
| 2006/0293722 | A1 | 12/2006 | Slatkine et al. |
| 2007/0021733 | A1 | 1/2007 | Hansen et al. |
| 2007/0049865 | A1 | 3/2007 | Radmer et al. |
| 2007/0073228 | A1 | 3/2007 | Mernoe et al. |
| 2007/0118405 | A1 | 5/2007 | Campbell et al. |
| 2007/0167912 | A1 | 7/2007 | Causey et al. |
| 2007/0185449 | A1 | 8/2007 | Mernoe |
| 2007/0197968 | A1 | 8/2007 | Pongpairochana et al. |
| 2007/0203454 | A1 | 8/2007 | Shermer et al. |
| 2007/0233038 | A1* | 10/2007 | Pruitt ............... A61M 5/31586 604/522 |
| 2007/0282269 | A1 | 12/2007 | Carter et al. |
| 2008/0021439 | A1 | 1/2008 | Brittingham et al. |
| 2008/0033367 | A1 | 2/2008 | Haury et al. |
| 2008/0033369 | A1 | 2/2008 | Kohlbrenner et al. |
| 2008/0033393 | A1 | 2/2008 | Edwards et al. |
| 2008/0051711 | A1 | 2/2008 | Mounce et al. |
| 2008/0051730 | A1 | 2/2008 | Bikovsky |
| 2008/0059133 | A1 | 3/2008 | Edwards et al. |
| 2008/0097381 | A1* | 4/2008 | Moberg ............... A61M 5/1413 604/506 |
| 2008/0108951 | A1 | 5/2008 | Jerde et al. |
| 2008/0140006 | A1 | 6/2008 | Eskuri et al. |
| 2008/0140018 | A1 | 6/2008 | Enggaard et al. |
| 2008/0147004 | A1 | 6/2008 | Mann et al. |
| 2008/0167641 | A1 | 7/2008 | Hansen et al. |
| 2008/0188813 | A1 | 8/2008 | Miller et al. |
| 2008/0208138 | A1 | 8/2008 | Lim et al. |
| 2008/0215006 | A1 | 9/2008 | Thorkild |
| 2008/0215015 | A1 | 9/2008 | Cindrich et al. |
| 2008/0243087 | A1 | 10/2008 | Enggaard et al. |
| 2008/0249473 | A1 | 10/2008 | Rutti et al. |
| 2008/0262436 | A1 | 10/2008 | Olson |
| 2008/0269687 | A1 | 10/2008 | Chong et al. |
| 2008/0269723 | A1 | 10/2008 | Mastrototaro et al. |
| 2008/0274630 | A1 | 11/2008 | Shelton et al. |
| 2008/0294143 | A1 | 11/2008 | Tanaka et al. |
| 2008/0306449 | A1 | 12/2008 | Kristensen et al. |
| 2008/0312601 | A1 | 12/2008 | Cane |
| 2008/0319416 | A1 | 12/2008 | Yodfat et al. |
| 2009/0041805 | A1 | 2/2009 | Walker |
| 2009/0048347 | A1 | 2/2009 | Cohen et al. |
| 2009/0054750 | A1 | 2/2009 | Jennewine |
| 2009/0069784 | A1 | 3/2009 | Estes et al. |
| 2009/0076453 | A1 | 3/2009 | Mejlhede et al. |
| 2009/0088694 | A1 | 4/2009 | Carter et al. |
| 2009/0088731 | A1 | 4/2009 | Campbell et al. |
| 2009/0093792 | A1 | 4/2009 | Gross et al. |
| 2009/0093793 | A1 | 4/2009 | Gross et al. |
| 2009/0105650 | A1 | 4/2009 | Wiegel et al. |
| 2009/0124977 | A1 | 5/2009 | Jensen |
| 2009/0143730 | A1 | 6/2009 | De Polo et al. |
| 2009/0143735 | A1 | 6/2009 | De Polo et al. |
| 2009/0149830 | A1 | 6/2009 | Spector |
| 2009/0182277 | A1 | 7/2009 | Carter |
| 2009/0204076 | A1 | 8/2009 | Liversidge |
| 2009/0209896 | A1 | 8/2009 | Selevan |
| 2009/0234319 | A1 | 9/2009 | Marksteiner |
| 2009/0240240 | A1 | 9/2009 | Hines et al. |
| 2009/0253973 | A1 | 10/2009 | Bashan et al. |
| 2009/0259176 | A1 | 10/2009 | Yairi |
| 2009/0281585 | A1 | 11/2009 | Katzman et al. |
| 2009/0299290 | A1 | 12/2009 | Moberg |
| 2009/0299397 | A1 | 12/2009 | Ruan et al. |
| 2009/0326459 | A1 | 12/2009 | Shipway et al. |
| 2009/0326509 | A1 | 12/2009 | Muse et al. |
| 2010/0030156 | A1 | 2/2010 | Beebe et al. |
| 2010/0030198 | A1 | 2/2010 | Beebe et al. |
| 2010/0049128 | A1 | 2/2010 | McKenzie et al. |
| 2010/0049144 | A1 | 2/2010 | McConnell et al. |
| 2010/0057057 | A1 | 3/2010 | Hayter et al. |
| 2010/0076412 | A1 | 3/2010 | Rush et al. |
| 2010/0094255 | A1 | 4/2010 | Nycz et al. |
| 2010/0100076 | A1 | 4/2010 | Rush et al. |
| 2010/0100077 | A1 | 4/2010 | Rush et al. |
| 2010/0106098 | A1* | 4/2010 | Atterbury ......... A61M 5/31566 604/207 |
| 2010/0121314 | A1 | 5/2010 | Iobbi |
| 2010/0137790 | A1 | 6/2010 | Yodfat |
| 2010/0137831 | A1 | 6/2010 | Tsals |
| 2010/0145303 | A1 | 6/2010 | Yodfat et al. |
| 2010/0145305 | A1 | 6/2010 | Alon |
| 2010/0162548 | A1 | 7/2010 | Leidig |
| 2010/0168607 | A1 | 7/2010 | Miesel |
| 2010/0168683 | A1 | 7/2010 | Cabiri |
| 2010/0198157 | A1 | 8/2010 | Gyrn et al. |
| 2010/0204657 | A1 | 8/2010 | Yodfat et al. |
| 2010/0234767 | A1 | 9/2010 | Sarstedt |

(56) References Cited

U.S. PATENT DOCUMENTS

| | | |
|---|---|---|
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | | |
|---|---|---|---|
| CN | 101090749 A | 12/2007 | |
| CN | 201941304 U | 8/2011 | |
| CN | 102186733 A | 9/2011 | |
| DE | 1064693 B | 9/1959 | |
| EP | 0017412 A1 | 10/1980 | |
| EP | 0222656 A1 | 5/1987 | |
| EP | 0401179 A1 | 12/1990 | |
| EP | 1530979 A1 | 5/2005 | |
| EP | 1666080 A1 | 6/2006 | |
| EP | 2060606 A1 | 5/2009 | |
| EP | 2498589 A1 | 9/2012 | |
| GB | WO 2009136209 A1 * | 11/2009 | ............ A61M 5/20 |
| JP | H07-194701 A | 8/1995 | |
| JP | H09-505758 A | 6/1997 | |
| JP | 2001-512992 A | 8/2001 | |
| JP | 2002-505601 A | 2/2002 | |
| JP | 2002-507459 A | 3/2002 | |
| JP | 2002-528676 A | 9/2002 | |
| JP | 2003-501157 A | 1/2003 | |
| JP | 2003-527138 A | 9/2003 | |
| JP | 2003-534061 A | 11/2003 | |
| JP | 2004-501721 A | 1/2004 | |
| JP | 2004-512100 A | 4/2004 | |
| JP | 2005-523127 A | 8/2005 | |
| JP | 2005-270629 A | 10/2005 | |
| JP | 2007-509661 A | 4/2007 | |
| JP | 2008-534131 A | 8/2008 | |
| JP | 2008-220961 A | 9/2008 | |
| JP | 2009-502273 A | 1/2009 | |
| WO | 9009202 A1 | 8/1990 | |
| WO | 9307922 A1 | 4/1993 | |
| WO | 9407553 A1 | 4/1994 | |
| WO | 9513838 A1 | 5/1995 | |
| WO | 9609083 A1 | 3/1996 | |
| WO | 9632975 A1 | 10/1996 | |
| WO | 9700091 A1 | 1/1997 | |
| WO | 9710012 A1 | 3/1997 | |
| WO | 9733638 A1 | 9/1997 | |
| WO | 9857683 A1 | 12/1998 | |
| WO | 9929151 A1 | 6/1999 | |
| WO | 9959665 A1 | 11/1999 | |
| WO | 0025844 A1 | 5/2000 | |
| WO | 0187384 A1 | 11/2001 | |
| WO | 0189607 A2 | 11/2001 | |
| WO | 0189613 A1 | 11/2001 | |
| WO | 0202165 A2 | 1/2002 | |
| WO | 0234315 A1 | 5/2002 | |
| WO | 0272182 A1 | 9/2002 | |
| WO | 03090833 A1 | 11/2003 | |
| WO | 2004032990 A2 | 4/2004 | |
| WO | 2004105841 A1 | 12/2004 | |
| WO | 2005018703 A2 | 3/2005 | |
| WO | 2005037350 A2 | 4/2005 | |
| WO | 2006037434 A1 | 4/2006 | |
| WO | 2006069380 A1 | 6/2006 | |
| WO | 2006102676 A1 | 9/2006 | |
| WO | 2006104806 A2 | 10/2006 | |
| WO | 2007051563 A1 | 5/2007 | |
| WO | 2007056504 A1 | 5/2007 | |
| WO | 2008001377 A2 | 1/2008 | |
| WO | 2008014908 A1 | 2/2008 | |
| WO | 2008057976 A2 | 5/2008 | |
| WO | 2008072229 A2 | 6/2008 | |
| WO | 2008076459 A1 | 6/2008 | |
| WO | 2008078318 A2 | 7/2008 | |
| WO | 2009044401 | 4/2009 | |

(56) References Cited

FOREIGN PATENT DOCUMENTS

| WO | 2009046989 A2 | 4/2009 | | |
|---|---|---|---|---|
| WO | 2009125398 A2 | 10/2009 | | |
| WO | WO 2009136209 A1 * | 11/2009 | ............. | A61M 5/20 |
| WO | 2009144085 A2 | 12/2009 | | |
| WO | 2010078227 A1 | 7/2010 | | |
| WO | WO 2010078242 A1 * | 7/2010 | ............. | A61K 8/64 |
| WO | 2011075105 A1 | 6/2011 | | |
| WO | 2011090955 A1 | 7/2011 | | |
| WO | 2011090956 A2 | 7/2011 | | |
| WO | 2011156373 A1 | 12/2011 | | |
| WO | 2012032411 A2 | 3/2012 | | |
| WO | 2012040528 A1 | 3/2012 | | |
| WO | 2012160157 A1 | 11/2012 | | |

OTHER PUBLICATIONS

Copaxone®, Manufactured by Teva Pharmaceutical Industries Ltd.
Int'l Search Report issued May 13, 2009 in Int'l Application No. PCT/IL2008/001312.
Int'l Preliminary Report on Patentability issued Apr. 7, 2010 in Int'l Application No. PCT/IL2008/001312; Written Opinion.
Int'l Search Report issued Apr. 26, 2010 in Int'l Application No. PCT/US2009/069552.
Office Action issued Apr. 5, 2010 in U.S. Appl. No. 12/244,666.
Office Action issued Sep. 21, 2010 in U.S. Appl. No. 12/244,666.
Office Action issued Apr. 5, 2010 in U.S. Appl. No. 12/244,688.
Office Action issued Sep. 2, 2010 in U.S. Appl. No. 12/244,688.
Office Action issued Sep. 30, 2010 in U.S. Appl. No. 12/689,250.
Int'l Search Report issued Jan. 12, 2011 in Int'l Application No. PCT/US2010/048556; Written Opinion.
U.S. Appl. No. 60/997,459, filed Oct. 2, 2007.
International Preliminary Report on Patentability issued on Jul. 5, 2011 in International Application No. PCT/US2009/069552; Written Opinion.
Office Action issued Jul. 13, 2011 in U.S. Appl. No. 12/559,563.
Int'l Preliminary Report on Patentability issued Sep. 1, 2011 in Int'l Application No. PCT/US2010/048556.
Office Action issued Sep. 6, 2011 in U.S. Appl. No. 12/345,818.
Office Action issued Feb. 21, 2012 in U.S. Appl. No. 12/689,249.
Int'l Search Report issued Jun. 17, 2011 in Int'l Application No. PCT/US2011/021604.
Int'l Search Report issued Oct. 12, 2011 in Int'l Application No. PCT/US2011/021605.
Office Action issued Oct. 28, 2011 in U.S. Appl. No. 12/615,828.
Int'l Search Report issued Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action issued May 16, 2012 in U.S. Appl. No. 12/615,828.
Office Action issued Jul. 2, 2012 in U.S. Appl. No. 13/272,555.
Office Action issued May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability issued Aug. 2, 2012 in Int'l Application No. PCT/US2011/021604.
Office Action issued Oct. 9, 2013 in IL Application No. 208634.
Office Action issued Nov. 5, 2013 in JP Application No. 2010-527595.
Office Action issued Sep. 29, 2013 in CN Application No. 201080040968.7.
Office Action issued Nov. 4, 2013 in EP Application No. 11 709 234.6.
U.S. Appl. No. 13/733,516 by Cabiri, filed Jan. 3, 2013.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
U.S. Appl. No. 13/874,017 by Cabiri, filed Apr. 30, 2013.
Office Action issued Dec. 17, 2013 in JP Application No. 2012-529808.
Office Action issued Dec. 10, 2013 in CN Application No. 201180006567.4.
Office Action issued Jan. 8, 2014 in U.S. Appl. No. 13/521,167 by Cabiri.
U.S. Appl. No. 29/479,307 by Norton, filed Jan. 14, 2014.
English translation of an Office Action issued Jan. 30, 2013 in CN Application No. 200880117084.X.
U.S. Appl. No. 14/193,692 by Gross, filed Feb. 28, 2014.
Office Action issued Feb. 4, 2014 in EP Application No. 11 707 942.6.
English translation of an Office Action issued Mar. 5, 2014 in CN Application No. 200880117084.X.
Int'l Search Report and Written Opinion issued Apr. 3, 2014 in Int'l Application No. PCT/US2013/078040.
Extended European Search Report issued Mar. 27, 2014 in EP Application No. 14154717.4.
Office Action issued Feb. 28, 2014 in CN Application No. 201180006571.0.
U.S. Appl. No. 14/258,661 by Cabiri, filed Apr. 22, 2014.
Int'l Search Report and Written Opinion issued Jan. 7, 2014 in Int'l Application No. PCT/US2013/065211.
Office Action issued May 23, 2014 in U.S. Appl. No. 13/472,112 by Cabiri.
Office Action issued Jun. 3, 2014 in JP Application No. 2010-527595.
Office Action issued Jul. 7, 2014 in U.S. Appl. No. 12/244,666 by Gross.
Int'l Search Report and Written Opinion issued Jul. 31, 2014 in Int'l Application No. PCT/US2014/033598.
Int'l Search Report and Written Opinion issued Jul. 26, 2013 in Int'l Application No. PCT/US2012/039465.
Int'l Search Report and Written Opinion issued Aug. 5, 2013 in Int'l Application No. PCT/US2013/033118.
U.S. Appl. No. 13/964,651 by Gross, filed Aug. 12, 2013.
Office Action issued Aug. 15, 2013 in CN Application No. 200880117084.X.
Office Action issued Jan. 8, 2013 in JP Application No. 2010-527595.
Int'l Preliminary Report on Patentability issued Feb. 7, 2013 in Int'l Application No. PCT/US2011/021604.
Int'l Preliminary Report on Patentability issued Feb. 7, 2013 in Int'l Application No. PCT/US2011/021605.
Extended European Search Report issued Aug. 7, 2014 in EP Application No. 1417477.4.
Office Action issued Aug. 6, 2014 in EP Application No. 11 707 942.6.
Office Action issued Sep. 2, 2014 in JP Application No. 2012-550069.
Office Action issued Sep. 2, 2014 in JP Application No. 2012-550068.
Office Action issued Aug. 26, 2014 in CN Application No. 201180006567.4.
Int'l Preliminary Report on Patentability issued Oct. 9, 2014 in Int'l Application No. PCT/US2013/033118.
Office Action issued Oct. 9, 2014 in U.S. Appl. No. 13/873,335.
U.S. Appl. No. 14/553,399 by Cabiri, filed Nov. 25, 2014.
Office Action issued Nov. 2, 2014 in CN Application No. 201180006571.0.
Office Action issued Nov. 21, 2014 in U.S. Appl. No. 13/472,112 by Cabiri.
Office Action issued Nov. 21, 2014 in U.S. Appl. No. 13/429,840 by Cabiri.
Int'l Preliminary Report on Patentability issued Nov. 27, 2014 in Int'l Application No. PCT/US2013/039465.
Int'l Preliminary Report on Patentability issued May 14, 2015 in Int'l Application No. PCT/US2013/065211.
Office Action issued May 7, 2015 in JP Application No. 2012-550069.
Office Action issued May 13, 2015 in CN Application No. 201380025566.3.
U.S. Appl. No. 14/715,791 by Cabiri, filed May 19, 2015.

(56) References Cited

OTHER PUBLICATIONS

U.S. Appl. No. 14/725,009 by Bar-El, filed May 29, 2015.
Office Action issued May 1, 2015 in U.S. Appl. No. 14/638,525 by Filman.
Office Action issued Jun. 4, 2015 in U.S. Appl. No. 13/667,739 by Cabiri.
U.S. Appl. No. 14/593,051 by Gross, filed Jan. 9, 2015.
Extended European Search Report issued Feb. 23, 2015 in EP Application No. 14166596.8.
Extended European Search Report issued Feb. 23, 2015 in EP Application No. 14166591.9.
Office Action issued Mar. 10, 2015 in CN Application No. 201180006567.4.
Office Action issued Mar. 31, 2015 in JP Application No. 2012-550068.
U.S. Appl. No. 14/683,193 by Cabiri, filed Apr. 10, 2015.
Office Action issued Feb. 20, 2015 in U.S. Appl. No. 13/521,181 by Cabiri.
Office Action issued Feb. 24, 2015 in U.S. Appl. No. 14/258,661 by Cabiri.
U.S. Appl. No. 14/638,525 by Filman, filed Mar. 4, 2015.
Office Action issued Mar. 10, 2015 in U.S. Appl. No. 12/244,666 by Gross.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action issued Sep. 30, 2015 in U.S. Appl. No. 13/667,739 by Cabiri.
Office Action issued Sep. 18, 2015 in U.S. Appl. No. 13/874,085 by Cabiri.
Office Action issued Jul. 31, 2015 in U.S. Appl. No. 13/521,181 by Cabiri.
Office Action issued Aug. 13, 2015 in U.S. Appl. No. 14/553,399 by Cabiri.
Notice of Allowance issued Aug. 24, 2015 in U.S. Appl. No. 29/479,307 by Norton.

\* cited by examiner

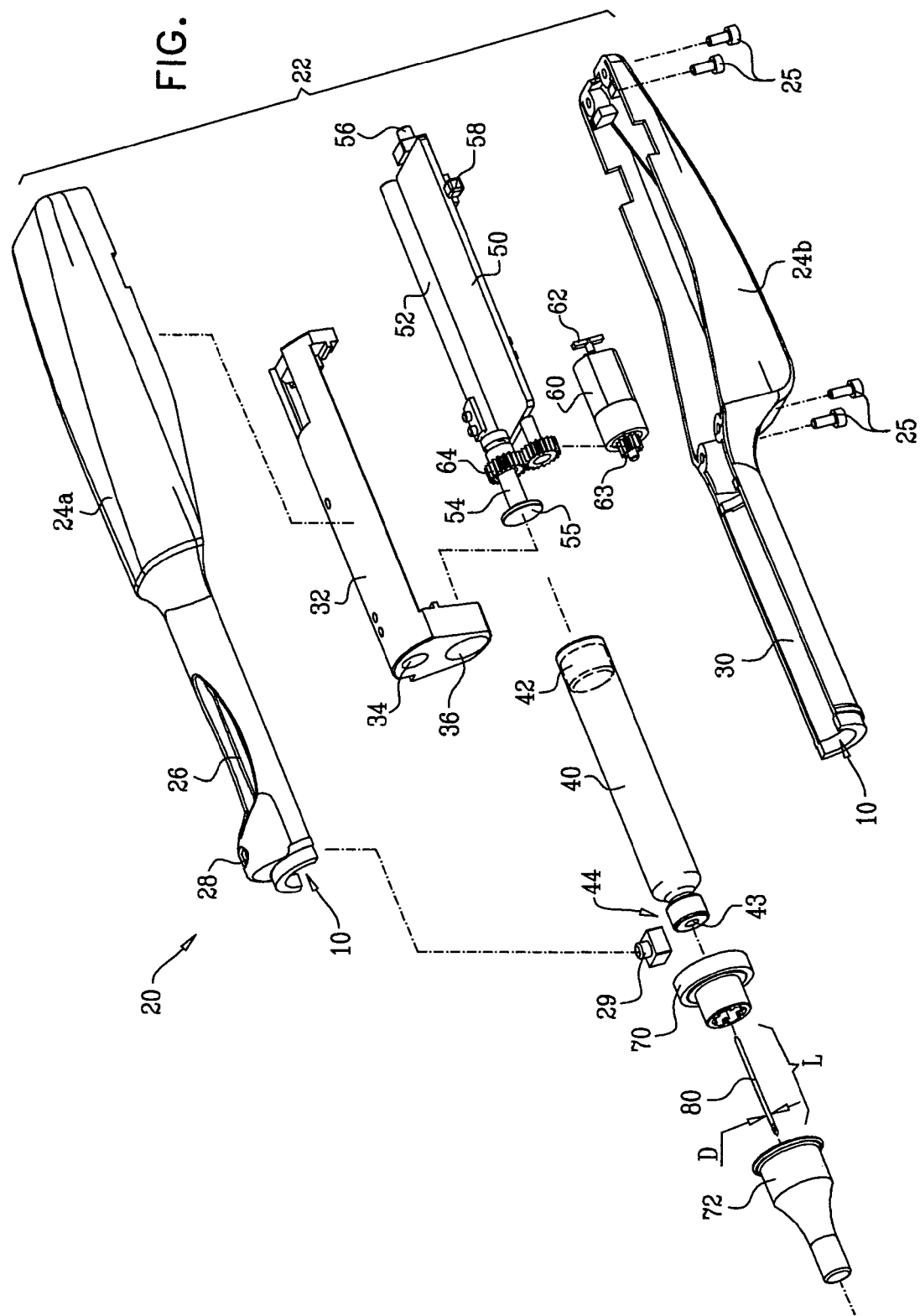

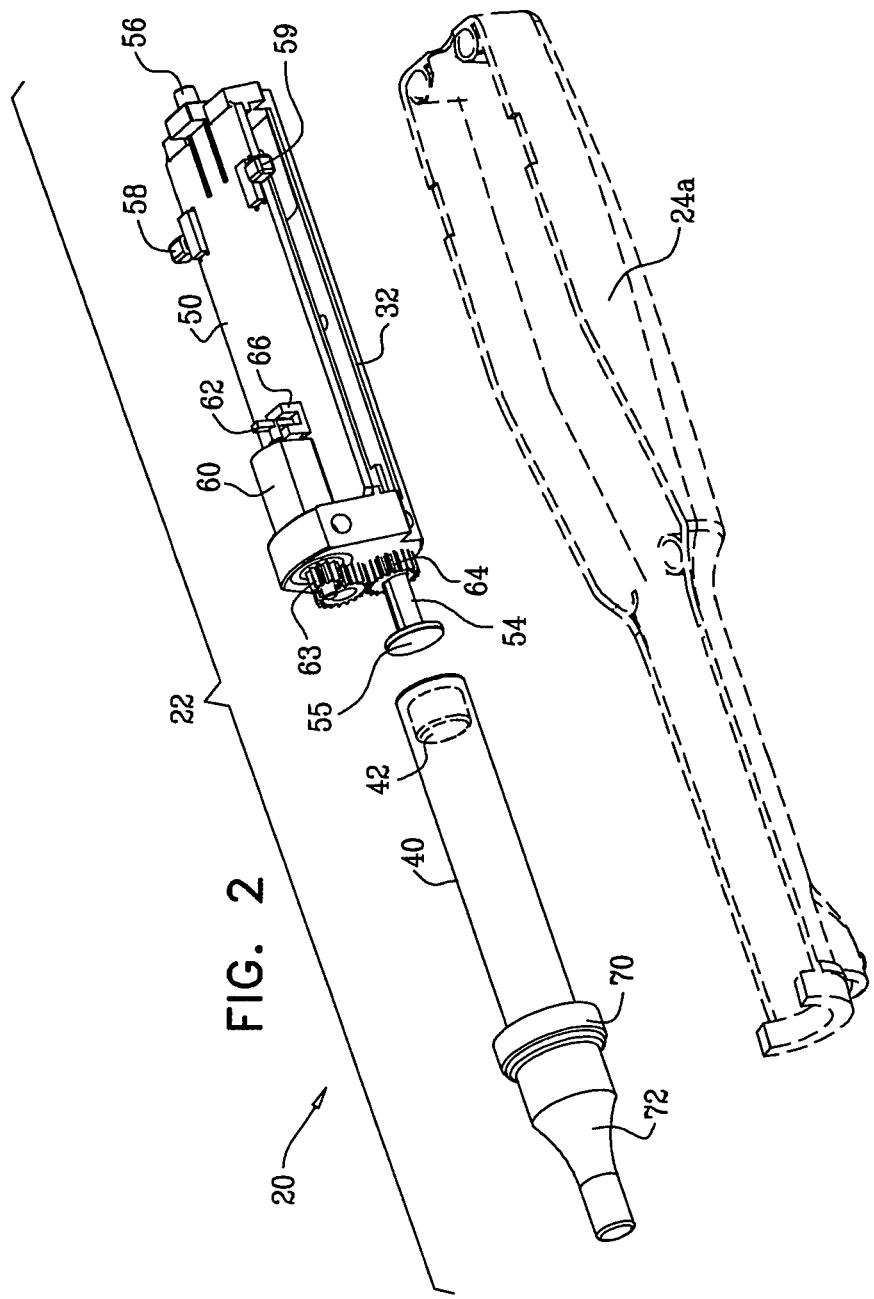

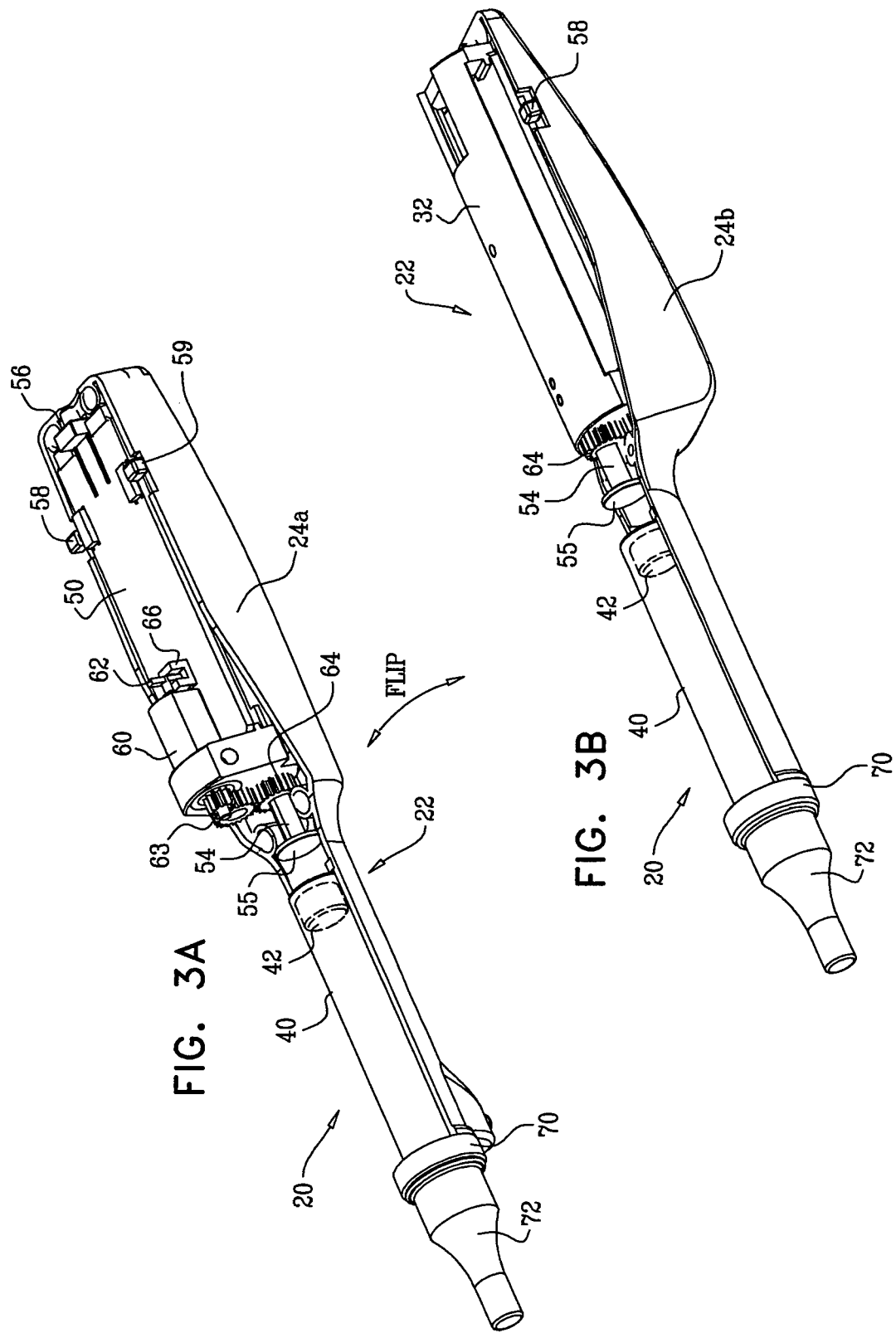

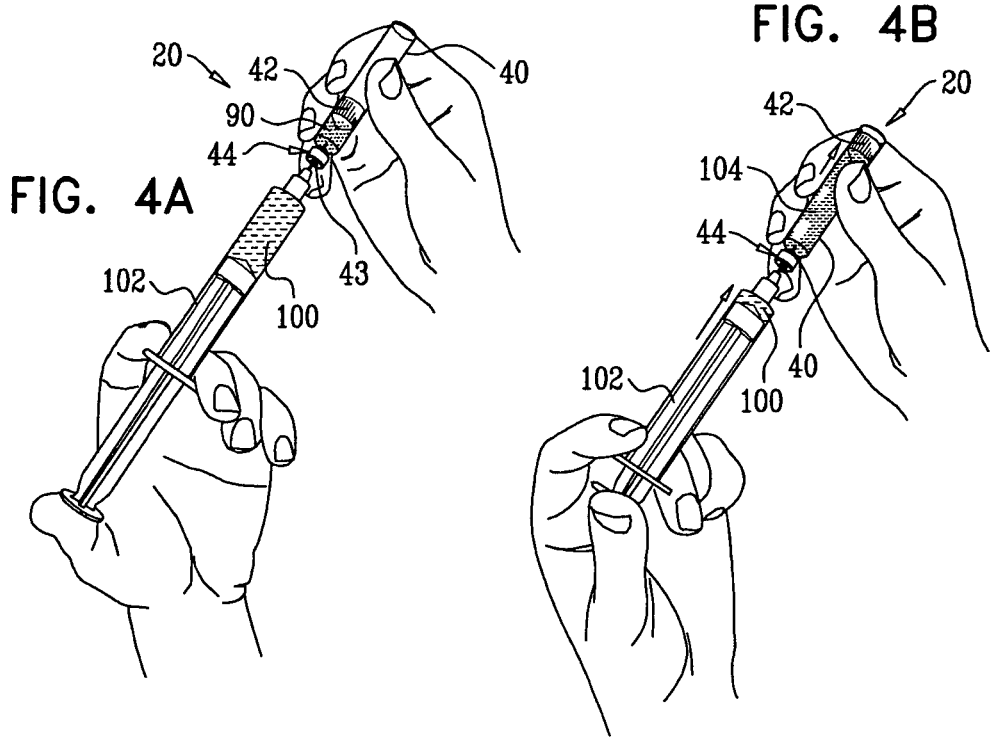
FIG. 4A
FIG. 4B
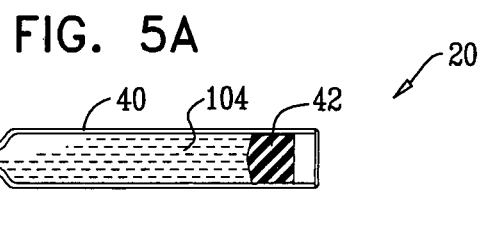
FIG. 5A
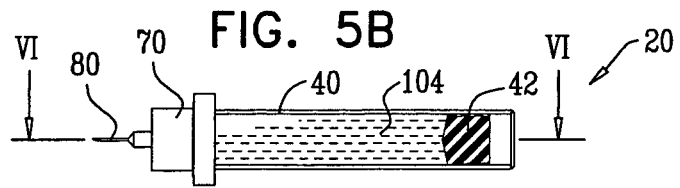
FIG. 5B
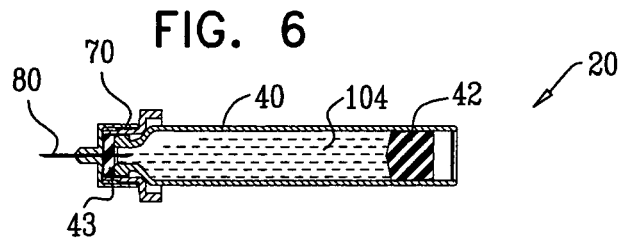
FIG. 6

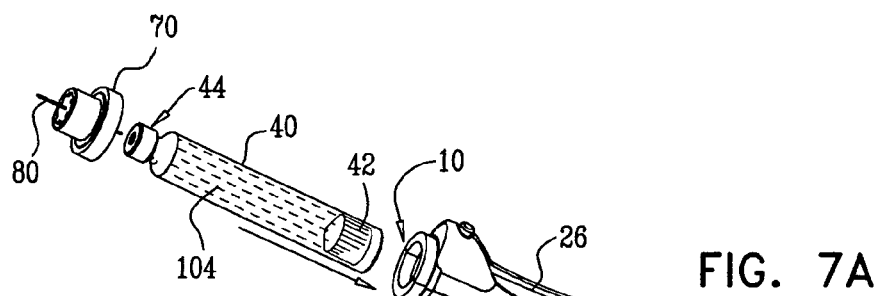
FIG. 7A
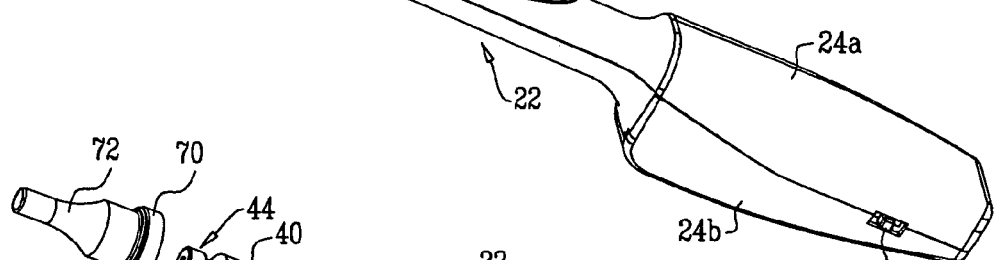
FIG. 7B
FIG. 8
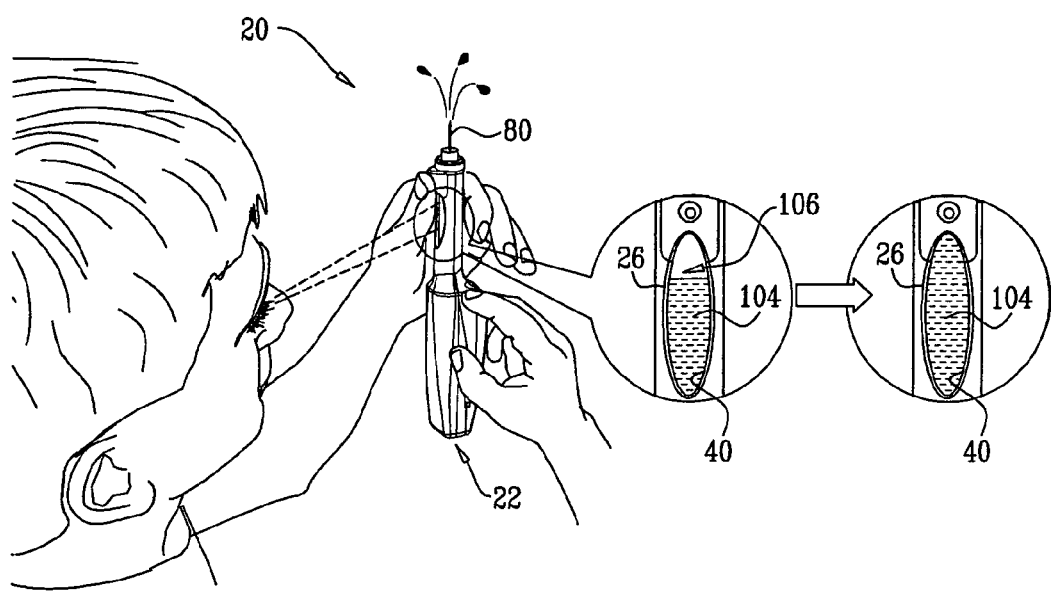

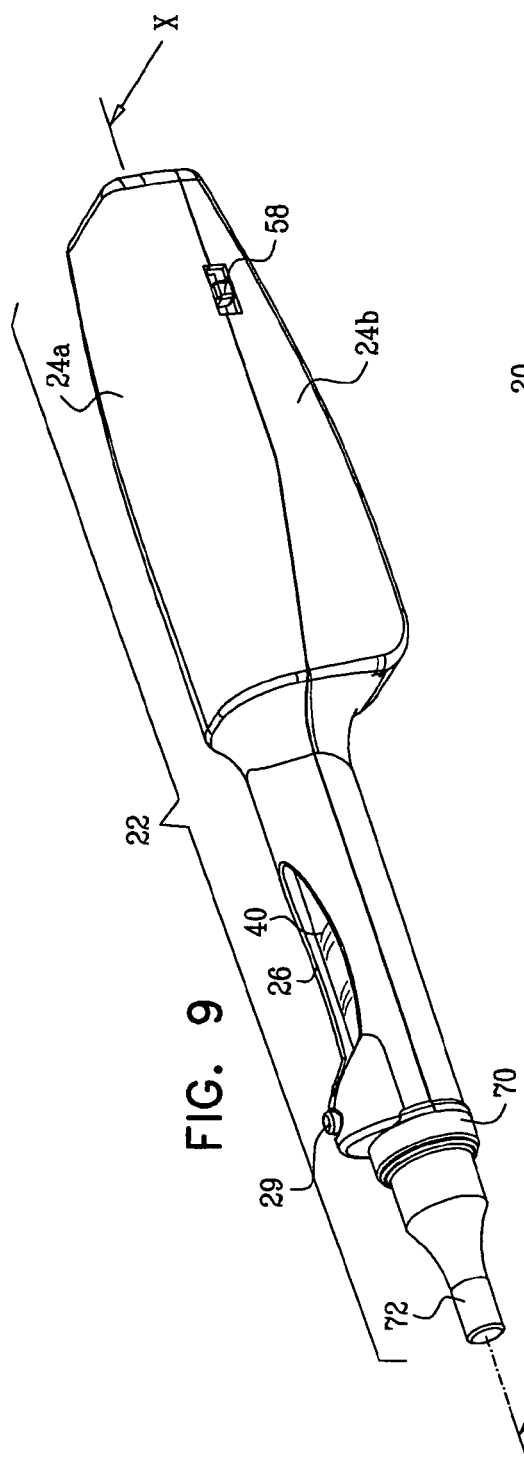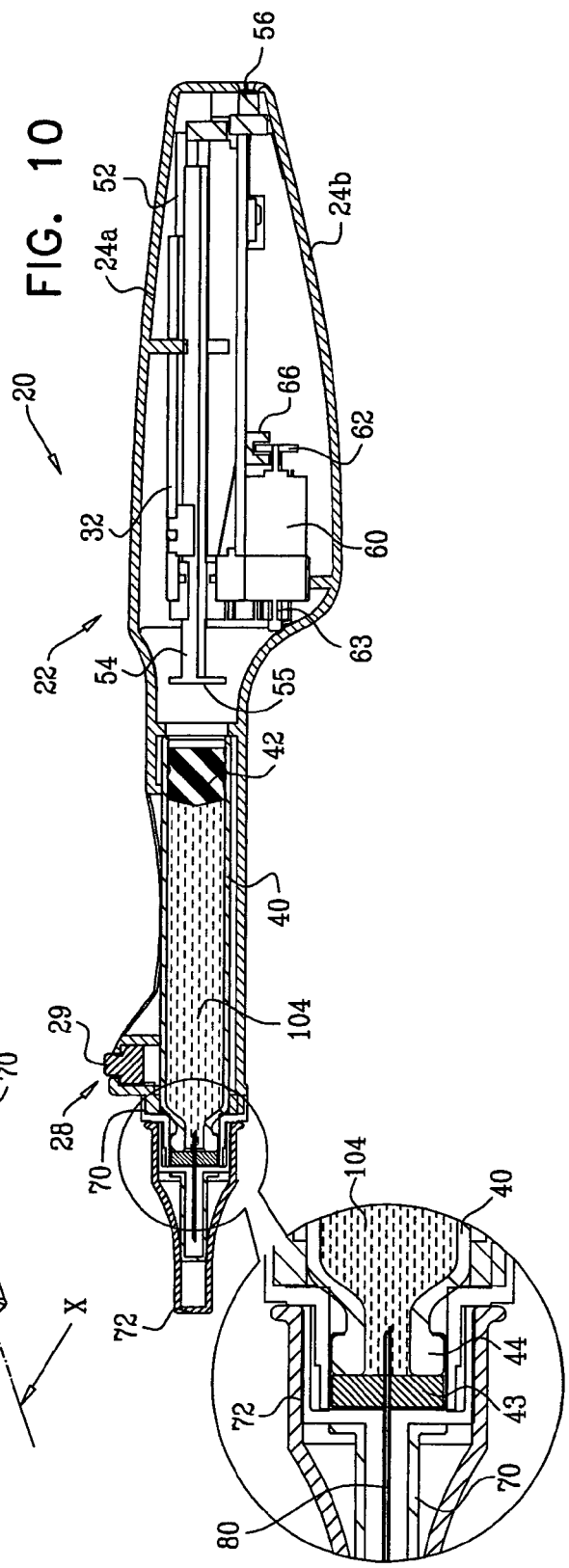

LOW VOLUME ACCURATE INJECTOR

CROSS-REFERENCE TO RELATED APPLICATION

This application is a section 371 of International Application No. PCT/IL2011/000368, filed May 8, 2011, which was published in the English language on Nov. 17, 2011 under International Publication No. WO 2011/141907 which claims the benefit of U.S. Provisional Patent Application No. 61/332,855, filed May 10, 2010, the disclosures of which are incorporated herein by reference.

The present application is related to U.S. patent application Ser. No. 12/615,828 to Alon entitled, "Low volume accurate injector," filed Nov. 10, 2009, which published as US 2010/0145305 and claims the priority of U.S. Provisional Patent Application 61/198,906 to Alon entitled, "Low volume accurate injector," filed Nov. 10, 2008.

All of these applications are incorporated herein by reference.

FIELD OF THE INVENTION

Applications of the present invention relate generally to substance administration, and specifically to apparatus and methods for administering cosmeceuticals and other drugs.

BACKGROUND OF THE INVENTION

Mesotherapy is described by Wikipedia as a non-surgical cosmetic medicine treatment. Mesotherapy employs multiple injections of pharmaceutical and homeopathic medications, plant extracts, vitamins, and other ingredients into the subcutaneous fat.

WO 08/057976 to Sibbitt et al. describes multiple dose syringe apparatus and methods which are described as being suitable for use to administer multiple small doses of drugs particularly for dermatology, plastic surgery, cosmetic surgery, and neurological medicine. The multiple dose syringes can be constructed from a conventional syringe and conventional plunger with adapters, and also by individual injection mounding.

WO 06/102676 to Perez et al. describes injectable implants that are described as being useful in supplementing soft tissue, particularly skin. The publication relates to dermal filler compositions of biocompatible polyethylene oxides that may be introduced, perhaps by injection, into areas of soft tissue often considered in need of augmentation. Examples include cosmetic enhancement or correction of facial defects due to scarring, aging and the like.

U.S. Pat. No. 3,794,028 to Mueller et al. describes a method of depilation in a human by injecting a dose of chemical depilatory solution into a hair follicle to permanently destroy hair growth at that location. Injection of the chemical depilatory solution may be effected by means of a hypodermic syringe for penetrating beneath the skin surface and for dispensing effective dosage amounts of the depilatory solution into the follicle.

U.S. Pat. No. 5,366,498 to Brannan et al. describes a device for correcting fine superficial facial lines, which comprises a syringe fitted with a 31-33 gauge needle and an aqueous suspension of non-crosslinked fibrillar atelopeptide collagen contained within the syringe barrel, the concentration of collagen in the suspension being in the range of 10 to 50 mg/ml, and the suspension exhibiting an extrusion plot in which there is a smooth substantially linear increase in force up to a substantially constant force in the range of 5 to 30 newtons.

U.S. Pat. No. 6,689,118 to Alchas et al. describes a method of performing an intradermal injection using a drug delivery device containing the substance to be injected. A device for practicing the method includes a needle cannula having a forward tip and a limiter portion having a skin engaging surface surrounding the needle cannula. The needle cannula is in fluid communication with the substance and the tip of the needle cannula extends beyond the skin engaging surface a distance equal to approximately 0.5 mm to 3.0 mm. The needle cannula includes a fixed angle of orientation relative to the plane of the skin engaging surface. The skin engaging surface limits penetration of the needle tip into the skin so that the substance can be expelled through the needle tip into the dermis layer. Preferably, the fixed angle of orientation of the needle cannula is generally perpendicular relative to the skin surface, and the skin engaging surface is generally flat.

US Patent Application Publication 2008/0262436 to Olson describes an injection device comprising a tubular elongated main body, a needle shield slidably arranged in said main body, a needle shield link slidably connected to said needle shield, a enclosure containing medicament arranged in said main body, a needle connected to said enclosure, a plunger operatively arranged to said enclosure for ejecting said medicament through said needle and arranged on its upper part with a number of outwardly extending stop members, spring means arranged to said plunger for operating said plunger, a dose activating means, a needle shield spring surrounding the needle shield link. The device is characterised in that said injection device further comprises a first tubular member rotationally and slidably arranged inside said needle shield link, said tubular member comprises a number or ridges and protrusions on both its outer and inner surfaces, said ridges and protrusions on the outer surface of the tubular member co-operate with guide members arranged on the inner surface of said needle shield link, said ridges and protrusions on the inner surface of the tubular member co-operate with the outwardly extending stop members of the plunger that said injection device further comprises a second tubular member arranged inside said housing, arranged and designed with a number of ridges and protrusions on its inner and outer surfaces capable of setting and delivering a certain preset dose.

U.S. Pat. No. 7,364,570 to Gerondale et al. describes a controlled volume injection/aspiration device includes a syringe having a body for containing a medicament, a needle and a piston slidably disposed within the body. A shell is provided for receiving the syringe body and a plunger rack is disposed within the shell. A manually operated control is disposed in an operative relationship with the plunger rack for moving the plunger rack in a stepwise forward direction causing the piston to eject discrete doses of medication from the syringe body through the needle. The manual operated control is also operative for moving the piston in a stepwise reverse direction causing the piston to aspirate fluid into the syringe body through the needle.

The following references may be of interest:
PCT Publication WO 08/072229 to Levin et al.
U.S. Design Pat. D593,677 to Mudd et al.
U.S. Pat. No. 5,858,001 to Tsals et al.
US Patent Application Publication 2008/0021439 to Brittingham et al.

An insulin pen is described by Wikipedia as an insulin injection system for the treatment of diabetes. A pen has a disposable needle, a vial of insulin, and the pen housing. To use a pen, the user screws on a new needle, turns a dial on the end of the pen to the number of units of insulin needed, and inserts the needle into the skin. She then presses a button on the end of the pen to deliver the selected dose, waits until the dose is delivered, and removes the needle.

SUMMARY OF EMBODIMENTS OF THE INVENTION

In some embodiments of the present invention, a hand-held device is provided which comprises a dosage regulator for regulating the dosage and speed of delivery of substances such as drugs, vitamins, amino acids, collagen, Botox™, viscous substances, and/or other substances to a treatment site on skin of a subject. The hand-held device is couplable to or is coupled to a needle which has a skin-insertion portion that is 0.3-2.5 mm in length, and an outer diameter that is less than 0.23 mm. The hand-held device accommodates variously sized cartridges containing various substances. Expulsion of the substances from the cartridge is controlled by the dosage regulator, which is actuated by a user. The electronic dosage regulator actuates the motor in a pulsatile manner so as to produce brief periods of high pressure in the device that expel a predetermined volume of the substance through the needle at a controlled rate. This pulsatile mode of operation of the device is particularly useful for regulating the pressure of a highly viscous substance, such as collagen and Botox™, as it passes through the needle. Because of this regulation in pressure, the device allows the use of small diameter needles, which reduces or eliminates discomfort associated with multiple injections, as are facilitated by the hand-held device.

The dosage is user-selectable by the user, who adjusts a setting of the dosage regulator. The dosage regulator provides a plurality of possible settings of the dosage, including at least one dosage that is less than or equal to 10 ul (microliters), and typically other dosages that are higher than this value. A user-activatable injection driver drives the substance through the needle.

Additionally, the hand-held device accommodates variously sized cartridges containing various substances. An example of such cartridge includes a vial of Botox™ powder which is applied to the hand-held device, and which functions as the cartridge. Once the vial of Botox™ powder is coupled to the device, a small-diameter needle is coupled to the device, and the device facilitates drawing of saline solution through the needle and into the vial in order to suspend the Botox™ powder. As such, the device eliminates a step in the Botox™ procedure of having to suspend the Botox™ powder externally to the delivery system.

There is therefore provided, in accordance with some applications of the present invention, substance-administration apparatus, including:

a housing;

a needle, couplable to the housing, having a skin-insertion portion 0.3-2.5 mm in length and an outer diameter that is less than 0.23 mm;

a dosage regulator coupled to the housing, which regulates a dosage of a substance injected in a single injection through the needle, the dosage being selectable in accordance with a setting of the dosage regulator to be one of a plurality of selectable dosages, the plurality of selectable dosages including at least one dosage that is less than or equal to 10 ul;

an injection driver, activatable by a user to drive the substance through the needle, and a motor coupled to the injection driver, the motor being actuated by the dosage regulator in a pulsatile manner so as to produce brief periods of high pressure in the apparatus that expel a predetermined volume of the substance through the needle at a controlled rate.

In some applications of the present invention, the skin-insertion portion is 1-2.5 mm in length.

In some applications of the present invention, the apparatus is generally cylindrical.

In some applications of the present invention, the plurality of selectable dosages includes at least one dosage that is greater than 10 ul.

In some applications of the present invention, the plurality of selectable dosages does not include any dosages that are greater than 50 ul.

In some applications of the present invention, the at least one dosage is 5-10 ul.

In some applications of the present invention, the at least one dosage is 1-5 ul.

In some applications of the present invention, the outer diameter of the needle is less than 0.21 mm.

In some applications of the present invention, the outer diameter of the needle is between 0.15 mm and 0.23 mm.

In some applications of the present invention, the substance includes a viscous substance, and the dosage regulator is configured to regulate the dosage of the viscous substance injected in the single injection through the needle.

In some applications of the present invention, the apparatus includes a cartridge, pre-filled with the substance, couplable to the housing, for providing the substance in a plurality of injections.

In some applications of the present invention, the needle is couplable to the housing by being couplable to the cartridge, and the needle and the cartridge are couplable to the housing by the user, prior to use of the apparatus.

In some applications of the present invention, the cartridge is pre-filled with powder of botulinum toxin, and the housing is configured to receive the cartridge and to facilitate suspension of the powder subsequently to the receiving of the cartridge.

In some applications of the present invention, the apparatus includes the substance, and the substance includes a depilatory agent.

There is additionally provided, in accordance with some applications of the present invention, a substance-administration method, including:

regulating a dosage of a substance by selecting one of a plurality of selectable dosages, the plurality of selectable dosages including at least one dosage that is less than or equal to 10 ul;

inserting a needle having an outer diameter that is less than 0.23 mm into skin of a subject to a depth of 0.3-2.5 mm;

expelling a predetermined volume of the substance through the needle at a controlled rate by producing brief periods of high pressure in a device used to administer the substance; and administering the substance at the selected dosage through the needle.

In some applications of the present invention, inserting the needle includes inserting the needle to a depth of 1-2.5 mm.

In some applications of the present invention, the plurality of selectable dosages further includes at least one dosage that is greater than 10 ul, and selecting includes selecting the at least one dosage that is greater than 10 ul.

In some applications of the present invention, the plurality of selectable dosages does not include any dosages that are greater than 50 ul, and selecting includes selecting a dosage from the plurality of selectable dosages that does not include any dosages that are greater than 50 ul.

In some applications of the present invention, the at least one dosage is 5-10 ul, and selecting includes selecting the at least one dosage that is 5-10 ul.

In some applications of the present invention, the at least one dosage is 1-5 ul, and selecting includes selecting the at least one dosage that is 1-5 ul.

In some applications of the present invention, the outer diameter of the needle is less than 0.21 mm, and inserting the needle includes inserting the needle that has an outer diameter that is less than 0.21 mm.

In some applications of the present invention, the substance includes a depilatory agent, and administering the substance includes administering the depilatory agent.

In some applications of the present invention, the substance includes a viscous substance, and administering the substance includes administering the viscous substance.

In some applications of the present invention, the method includes coupling to the needle a cartridge that is pre-filled with the substance, and providing the substance from the cartridge in a plurality of injections.

In some applications of the present invention, the cartridge is pre-filled with powder of botulinum toxin, and the method further includes receive suspending the powder prior to the providing the substance from the cartridge in the plurality of injections.

In some applications of the present invention, inserting the needle in the skin includes inserting the needle in at least one site selected from the group consisting of: skin of a face of the subject and skin of a neck of the subject.

In some applications of the present invention, inserting the needle in the at least one selected site includes inserting the needle and administering the substance at at least 5 sites.

In some applications of the present invention, inserting the needle in the at least one selected site includes inserting the needle at two sites separated by less than 1 mm.

There is also provided, in accordance with some applications of the present invention, a substance-administration method, including:

inserting a needle having an outer diameter that is less than 0.23 mm into skin of a subject to a depth of 0.3-2.5 mm;

expelling a predetermined volume of the substance through the needle at a controlled rate by producing brief periods of high pressure in a device used to administer the substance; and administering the substance at the selected dosage through the needle.

The present invention will be more fully understood from the following detailed description of embodiments thereof, taken together with the drawing, in which:

BRIEF DESCRIPTION OF THE DRAWING

FIG. 1 is a schematic illustration of an exploded view of a hand-held device comprising an electronic dosage regulator and a small needle couplable to the hand-held device, the device being configured for administration of substances to a subject, in accordance with some applications of the present invention;

FIG. 2 is a schematic illustration of a portion of the hand-held device of FIG. 1, in accordance with some applications of the present invention;

FIGS. 3A-B are schematic illustrations of components of the hand-held device of FIG. 1, in accordance with some applications of the present invention;

FIGS. 4A-B are schematic illustrations of loading of a cartridge which is then coupled to the hand-held device of FIG. 1, in accordance with some applications of the present invention;

FIGS. 5A-B and 6 are schematic illustrations of coupling a needle to the cartridge of FIGS. 4A-B, in accordance with some applications of the present invention;

FIGS. 7A-B are schematic illustrations of the loading of the cartridge of FIGS. 4A-B into the hand-held device of FIG. 1;

FIG. 8 is a schematic illustration of preparing the hand-held device for use, in accordance with some applications of the present invention;

FIGS. 9 and 10 are schematic illustrations of the hand-held device of FIG. 1 ready for use, in accordance with some applications of the present invention;

FIG. 11 is a schematic illustration of use of the hand-held device of FIG. 1, in accordance with some applications of the present invention;

FIGS. 12A-B are schematic illustrations of the hand-held device of FIG. 1 following use, in accordance with some applications of the present invention; and FIG. 13 is a schematic illustration of the loading of the hand-held device of FIG. 1, in accordance with some other applications of the present invention.

DETAILED DESCRIPTION OF EMBODIMENTS OF THE INVENTION

Reference is now made to FIG. 1, which is a schematic illustration of apparatus 20 for administering a substance, comprising a hand-held housing 22, a needle 80 couplable to housing 22, and, typically, a cartridge 40, e.g., a vial, designated for containing the substance, in accordance with some applications of the present invention. Needle 80 comprises a very-fine needles which has a skin-insertion portion that has a length of 0.3-2.5 mm (e.g., 1-2.5 mm), and an outer diameter D that is less than 0.23 mm, e.g., less than 0.21 mm. For some embodiments, outer diameter D is between 0.15 mm and 0.23 mm. For example, needle 80 may comprise a 32 or 33 gauge needle, or one or more microneedles. The overall length L of needle 80 is between 0.6 and 5 mm. At least the distal portion of housing 22 is generally cylindrical. An electronic dosage regulator 60 is coupled to housing 22, and regulates a dosage of the substance injected in a single injection through needle 80. The dosage is user selectable by a user, who adjusts a setting of the dosage regulator. The dosage regulator provides a plurality of possible settings of the dosage. The dosage range includes at least one dosage that is less than or equal to 10 ul (microliters), e.g., 1-5 ul or 5-10 ul, but may also include dosages that are higher than this value, e.g., greater than 10 ul. Typically, the plurality of selectable dosages does not include any dosages that are greater than 50 ul. Dosage regulator 60 typically comprises a motor (e.g., a stepper motor or a DC motor) and an electronic panel which displays to the user information relating to the dosage. In such an application, dosage regulator 60 comprises a user interface 58 (e.g., a knob or a button) for the user to set the dosage, volume, and/or the speed of delivery of the dosage. The motor of electronic dosage regulator 60 facilitates pulsatile delivery of the viscous substance within cartridge 40, through needle 80, thereby minimizing pressure through the small needle 80 which would otherwise build up in needle 80 without such pulsatile delivery of the substance through needle 80 by the motor of regulator 60.

Hand-held housing 22 comprises an upper body portion 24a and a lower body portion 24b. Upper and lower body portions 24a and 24b are held together by screws 25. A panel 50 is disposed within housing 22 which comprises a structural component and electronics to transfer signals from user interface 58 and a reset button 56 toward regulator 60 coupled to panel 50. The motor of regulator 60 is coupled to a rotator 63 which is in turn coupled to a gear system 64. Gear system 64 actuates the displacement of an injection driver 54. When the user activates apparatus 20 via an actuation button 29 located at an upper portion 28 of housing 22, dosage regulator 60 activates the motor which activates injection driver 54. Regulator 60 actuates the motor in a pulsatile manner so as to produce brief periods of high pressure in apparatus 20 that expel a predetermined volume of the substance through needle 80 at a controlled rate. Every time the user presses actuation button 29, the motor of dosage regulator 60 runs and expels the substance within cartridge 40 through needle 80 by a predetermined, controlled amount. The user may release button 29 when he or she determines sufficient injection to a given area has been achieved.

Injection driver 54 comprises a flat surface 55 which pushes against a plunger 42 disposed within cartridge 40. An elongate rod is coupled to flat surface 55 and slides within a cylindrical housing 52 coupled to panel 50. A structural component 32 is disposed between panel 50 and upper body portion 24a. Structural component 32 is shaped so as to define a first hole 34 which enables passage therethrough of the rod of driver 54 while restricting proximal passage of flat surface 55 of driver 54. Additionally, structural component 32 is shaped so as to define a second hole 36 which enables rotation of rotator 63.

Typically, the motor of dosage regulator 60 is coupled to driver 54 and regulates (1) the speed of movement of driver 54 and (2) the distance driver 54 moves with each injection in order to control the dosage delivered to the treatment site with each injection. The motor is connected to a rotating indicator 62 which indicates the number of rotations of the motor, as is described hereinbelow.

For some embodiments of the present invention, a pre-filled cartridge 40 is couplable to housing 22 by being fed (e.g., slid) into an opening 10 at a distal end of housing 22 (the end of housing 22 that is closest to the skin of the user during the injection of the substance). Typically, the pre-filled cartridge 40 provides the substance to the user in a plurality of injections, e.g., for administration at at least 5 sites of tissue of a subject being administered the substance. For some embodiments, two injection sites are separated by less than 1 mm.

Alternatively, cartridge 40 is coupled to housing 22 without having been pre-filled with the substance. Prior to use, cartridge 40 is loaded with the substance to be administered, e.g., by drawing proximally injection driver 54, as described hereinbelow.

For some embodiments, prior to use of apparatus 20, cartridge 40 is couplable to needle 80 at a distal end of cartridge 40 (e.g., when needle 80 punctures a septum 43 at a distal end 44 of cartridge 40), and then cartridge 40 and needle 80 are couplable to (e.g., slid into) housing 22 by the user, prior to use of apparatus 20. Needle 80 is typically held in place by a needle-holder 70. A cap 72 covers needle 80 when hand-held housing 22 is not being used. Cap 72 is couplable to needle holder 70. Cartridge 40 slides into concave surface 30 which holds cartridge 40. Cartridge 40 is visible through a window 26 at upper body portion 24a of housing 22. Window 26 enables a user to view the amount of substance that has exited cartridge 40 during use of apparatus.

As appropriate for a given application and administered substance, the dosage range may include at least one dosage that is 5-10 ul and/or at least one dosage that is 1-5 ul.

Injection driver 54 may comprise any user-activatable apparatus (e.g., a plunger, as shown) suitable for initiating and/or driving the movement of a substance through a needle into tissue of the subject.

The substance typically comprises one or more components for esthetic or medical treatment of the skin or near underlying tissue, such as adipose tissue. Apparatus 20 is particularly suitable for providing treatments to the face and neck, where known therapies (e.g., mesotherapy) have not provided satisfactory solutions in terms of dosage accuracy and minimization of pain. In particular, the needles in typical mesotherapy guns range from 30 gauge (0.305 mm outer diameter) to 26 gauge (0.457 mm), and frequently provide per-injection dosages of even as high as 100-200 ul. Mesotherapy guns are additionally generally too heavy and bulky to facilitate easy, accurate placement of the needle at a range of sites on the face or neck in close proximity to each other. The large dosages and large needles used in mesotherapy frequently result in leakage of the administered substance out of the injection site, meaning that control of the administered dosage is suboptimal.

Some applications of the present invention solve the problem of the inability of the prior art to adequately treat the face and neck by providing a device that is, for example, similar in general shape and user interface to an insulin pen, but with a significantly shorter needle than is used in an insulin pen. It is noted that, fundamentally, an insulin pen is designed to facilitate systemic delivery of a drug, and therefore has a long needle length, e.g., 5-12 mm. By contrast, in these embodiments of the present invention, the goal is to treat the upper layers of the skin—typically, within 0.3-2.0 mm of the surface, and therefore these embodiments of the invention utilize a significantly shorter needle, e.g., 0.3-2.5 mm in length.

As appropriate for a given application, the administered substance may comprise one or more of the following:

hyaluronic acid;

one or more vitamins (e.g., C, B10, B8, B9, I, B3 B6, B2, E, A, B12);

one or more minerals (e.g., calcium chloride, potassium chloride, magnesium sulphate, sodium acetate, sodium chloride, sodium dihydrogen phosphate);

one or more nucleic acids (e.g., deoxyadenosine, deoxycytidine, deoxyguanosine, deoxythymidine, methylcytosine);

one or more amino acids (e.g., Alainin, Arginine, Aspara-gine, Aspartic acid, Cystein, Glutamin, glutamic acid, glycine, histine, hydroxyproline, isoleucin, Leucine, Lysine, Methionine, Omithine, Phenylalanine, Prolin, Serine, Taurine, Threonin, Tryptophan, Tyrosine, Valine);

one or more coenzymes (e.g., cocarboxylase, coenzyme A, flavin adenine dinucleotide phosphate, nicotinamide adenine dinucleotide, nicotinamide adenine dinucleotide phosphate, uridine triphosphate);

one or more reducing agents (e.g., ascorbic acid, glutathione);

Botox™;

Collagen (cross-linked and not cross-linked);

growth hormone at homeopathic concentrations or greater; and other hormones at homeopathic concentrations or greater.

In some embodiments, apparatus 20 described hereinabove is used to administer a depilatory agent, such as caustic soda, directly into a hair follicle. Advantageously, the small needle diameter and length provided by these embodiments of the invention (e.g., 32 or 33 gauge, 0.3-2.5 mm in length) allows relatively painless and accurate administration of the depilatory agent.

FIG. 2 shows a view that has been flipped from the view as shown in FIG. 1, in accordance with some applications of the present invention. FIG. 2 shows the assembled state of the inner mechanism which couples dosage regulator 60, rotator 63, and gear assembly 64 to driver 54. Panel 50 is coupled to an actuator 66 which is coupled to indicator 62 and records the number or rotations of indicator 62. Actuator 66 quantifies the number of rotations of indicator 62 and transfers the information to a display, thereby indicating the advancement of driver 54 within cartridge 40. For some applications, actuator provides an audible indication of the advancement of driver 54 within cartridge 40. Panel 50 is coupled and electronically coupled to a second user interface 59, e.g., a switch, which, when enabled by the user, turns on or off apparatus 20. Upper body portion 24a is shown in phantom to indicate the flipped view of apparatus 20 in FIG. 2.

As shown, flat surface 55 of driver 54 is disposed in communication with a proximal end of cartridge 40 and plunger 42 disposed therein. Cartridge 40 is shown coupled to needle holder 70 which is, in turn, coupled to cap 72.

FIG. 3A is identical to FIG. 2, as described hereinabove, with the exception that upper body portion 24a is shown as being coupled to the inner components of apparatus 20, in accordance with some applications of the present invention. FIG. 3A is shown without lower body portion 24b so as to show the inner components of apparatus 20.

FIG. 3B is a schematic illustration of a flipped view to the view shown in FIG. 3A, in accordance with some applications of the present invention. As shown, lower body portion 24b is shown as being coupled to the inner components of apparatus 20. FIG. 3b is shown without upper body portion 24a so as to show the inner components of apparatus 20.

FIGS. 4A-B show a user loading cartridge 40 with a solution 100, e.g., saline, prior to use of the hand-held device of apparatus 20, in accordance with some applications of the present invention. As shown, cartridge 40 contains a concentrated powder 90 (i.e., the substance to be injected into the user or by the user to a receiver of the substance) at a distal end and a plunger 42 disposed proximally to powder 90. As shown in FIG. 4A, the user holds in one hand a syringe 102 full of solution 100, and in the other hand holds cartridge 40. A needle coupled to syringe 102 punctures septum 43 at distal end 44 of cartridge 40 so as to facilitate injection of solution 100 into cartridge 40. As solution 100 is injected into cartridge 40, plunger 42 within cartridge 40 slides proximally, as shown in FIG. 4B, and a suspension 104 of powder 90 of the substance to be injected is created.

For some applications of the present invention, cartridge 40 contains Botox™ powder which is loaded with a solution prior to loading of cartridge into hand-held housing 22 of apparatus 20. That is, for such applications, cartridge 40 contains Botox™ powder 90 and a plunger 42. Cartridge 40 is typically disposable.

Reference is again made to FIGS. 4A-B. It is to be noted that cartridge 40 is shown as being loaded with solution 100 by way of illustration and not limitation, and that the scope of the present invention includes use of cartridges that are already pre-loaded with solution 100, i.e., cartridges that already contain suspension 104 of the substance to be injected.

FIGS. 5A-B and 6 show the coupling of needle 80 to cartridge 40, in accordance with some applications of the present invention. The loaded cartridge 40 with suspension 104 of the substance to be injected is coupled to needle holder 70 holding needle 80. Holder 70 is coupled to cartridge 40 at a distal end 44 of cartridge 40 by being screwed, or otherwise coupled to a distal end of hand-held housing 22. A proximal end of needle 80 punctures septum 43, as shown in the cross-sectional illustration in FIG. 6. As such, needle 80 accesses suspension 104 within cartridge 40.

FIGS. 7A-B show the loading of the pre-loaded, or pre-filled cartridge 40 within hand-held housing 22 of apparatus 20, in accordance with some applications of the present invention. As shown, cartridge 40 slides into opening 10 at the distal end of hand-held housing 22. It is to be noted that (1) needle holder 70 and needle 80 may be coupled to cartridge 40, and (2) cap 72 may be coupled to needle holder 72, at any stage before, during, and after loading of cartridge 40 into hand-held housing 22.

FIG. 8 shows expulsion of any air bubbles 106 within cartridge 40 following the loading of the pre-loaded, or pre-filled cartridge 40 within hand-held housing 22, in accordance with some applications of the present invention. The user removes cap 72 to expose the distal end of needle 80 and, viewing the air bubble 106 through window 26 of hand-held housing 22, activates apparatus 20 (i.e., by pushing on the on actuation button 29, as described hereinabove) to expel air bubble 106 from cartridge 40.

FIGS. 9-11 show apparatus 20 loaded with cartridge 40, coupled to needle 80, and ready for use, in accordance with some applications of the present invention. FIG. 9 shows an isometric view of the hand-held device of apparatus 20, and FIG. 10 shows a cross-sectional illustration of the hand-held device of apparatus 20, as described hereinabove. Prior to use, cap 72 is removed. Subsequently, apparatus 20 is turned on by interface 59 (not shown for clarity of illustration) and is set by interface 58 to one of three settings, as shown in FIG. 11. It is to be noted that any suitable number of settings may be selected by interface 58.

Reference is now made to FIGS. 10 and 11. FIG. 11 shows use of hand-held housing 22 of the hand-held device by a user. Prior to use, driver 54 and flat surface 55 ate disposed in their proximal-most position. During the actuation of apparatus 20, the user pushes on actuation button 29 which activates the motor of electronic dosage regulator 60. Activation of the motor effects rotation of rotator 63 which rotates gear assembly 64 to advance distally driver 54 which enters cartridge 40 at a proximal end thereof and pushes plunger 42 distally. As described hereinabove, the motor functions in a pulsatile manner transferring high burst of pressure to driver 54. In turn, driver 54 pushes plunger 42 to expel controlled amounts of suspension 104 containing the substance to be injected through needle 80. Use of the motor in the pulsatile manner at the proximal end of cartridge 40 reduces pressure at distal end 44 of cartridge 40 and through the very-fine needle 80 as the viscous substance is expelled from cartridge 40 and through needle 80. For some applications of the present invention apparatus 20 comprises a pressure sensor at the proximal end of hand-held housing 22 which measures the pressure of the viscous substances which exit the very-fine needle 80.

Figure 12A:
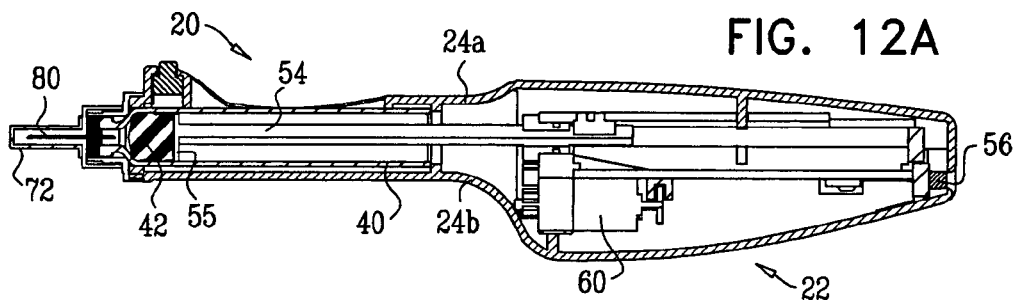

FIG. 12A shows apparatus 20 following use, in accordance with some applications of the present invention. As shown, cap 72 is again coupled to needle holder 70 in order to cover needle 80. Following use, plunger 42 is disposed at distal end 44 of cartridge 40 and flat surface 55 of driver 54 is disposed at a distal-most position.

Figure 12B:
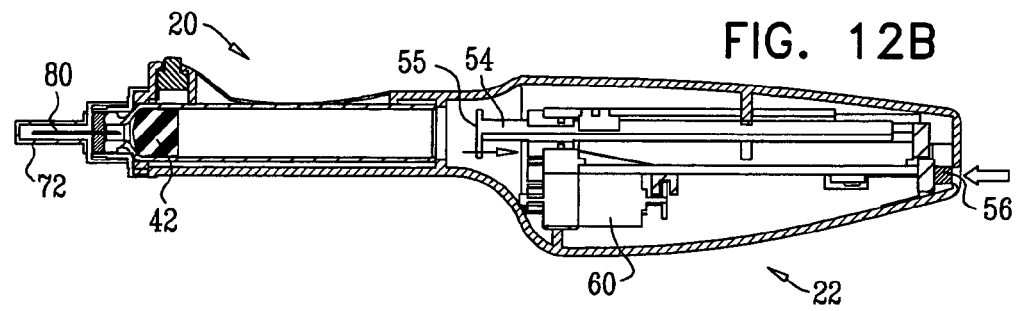

FIG. 12B shows resetting of apparatus 20 following use, in accordance with some applications of the present invention. The user pushes distally reset button 56 located at a proximal end of hand-held housing 22, typically by inserting a pin in an opening at the proximal end of hand-held housing 22. Pushing of reset button 56 pulls proximally driver 54 to its start position. Subsequently, needle holder 70 is decoupled from the distal end of hand-held housing 22, e.g., by being unscrewed therefrom, and the empty cartridge 40 is removed, e.g., by being slid distally through opening 10 of hand-held housing 22. Cartridge 40 is typically disposable.

Figure 13:
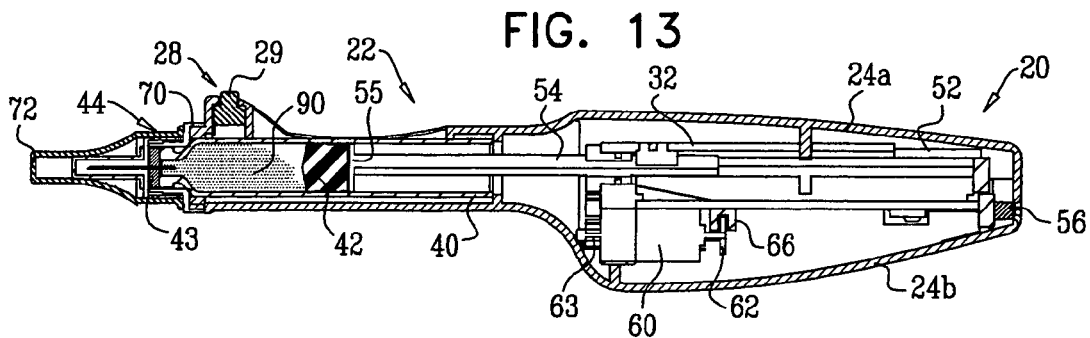

FIG. 13 is a schematic illustration of apparatus 22 prior to use in which a cartridge 40 containing powder 90 is disposed within hand-held housing 22, in accordance with some applications of the present invention. Following the coupling of cartridge 40 (i.e., by sliding cartridge 40 through opening 10 in hand-held housing 22, as described hereinabove), and following the coupling of needle 80 to cartridge 50 via needle holder 70, cartridge is then loaded with a solution in order to suspend powder 90. In such an embodiment, prior to use of apparatus 20, flat surface 55 driver 54 is reversibly coupled to plunger 42 of cartridge 40, e.g., by being magnetically coupled to plunger 42. That is, for such applications of the present invention, flat surface 55 is not disposed in its proximal-most position as described hereinabove.

As such, apparatus 20 eliminates a step in the Botox™ procedure of having to suspend the Botox™ powder externally to the delivery system.

The user then takes a vial of solution and punctures the vial with needle 80, now coupled to cartridge 40 and thereby to hand-held housing 22. The user activates apparatus 20 such that it functions in a manner reverse to the manner as described hereinabove, so as to move driver 54 proximally (thereby move plunger 42 proximally) in order to draw the solution into cartridge 40 and suspend powder 90 disposed within cartridge 40. Apparatus 20 is then actuated to operate as described hereinabove with reference to FIGS. 10 and 11, so as to expel in a controlled manner and with reduced pressure the suspension of powder 90 through needle 80 and inject the substance into the receiver of the substance. For some applications, powder 90 comprises Botox™ powder by way of illustration and not limitation. It is to be noted that powder 90 may comprise powder of any of the designated-for-injection substances listed herein.

For some applications, techniques described herein are practiced in combination with techniques described in one or more of the references cited in the Background section and Cross-references section of the present patent application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A substance-administration apparatus, comprising:

a housing;

a needle, couplable to the housing, having a skin-insertion portion 0.3-2.5 mm in length and an outer diameter that is less than 0.23 mm;

a dosage regulator coupled to the housing, which regulates a dosage of a substance expelled in a single injection through the needle, a single dosage from a plurality of selectable dosages being selectable by a user, the plurality of selectable dosages including at least one dosage that is less than or equal to 10 ul;

an electromechanical motor automatically actuated by the dosage regulator in a pulsatile manner, the motor being drivingly coupled to a rotator, which rotates about a central axis thereof;

an injection driver for driving the substance through the needle, the injection driver having a rotatable gear system drivingly coupled to the rotator;

wherein actuation of the motor in the pulsatile manner rotates the rotator and the coupled gear system in the pulsatile manner, to, in turn, drive the injection driver in the pulsatile manner to automatically produce a series of bursts of pressure in the housing that expel the single selected dosage of the substance through the needle at a controlled rate.

2. The apparatus according to claim 1, wherein the skin-insertion portion is 1-2.5 mm in length.

3. The apparatus according to claim 1, wherein the apparatus is generally cylindrical.

4. The apparatus according to claim 1, wherein the plurality of selectable dosages includes at least one dosage that is greater than 10 ul.

5. The apparatus according to claim 1, wherein the plurality of selectable dosages does not include any dosages that are greater than 50 ul.

6. The apparatus according to claim 1, wherein the at least one dosage is 5-10 ul.

7. The apparatus according to claim 1, wherein the at least one dosage is 1-5 ul.

8. The apparatus according to claim 1, wherein the outer diameter of the needle is less than 0.21 mm.

9. The apparatus according to claim 1, wherein the outer diameter of the needle is between 0.15 mm and 0.23 mm.

10. The apparatus according to claim 1, wherein the substance includes a viscous substance, and wherein the dosage regulator is configured to regulate the dosage of the viscous substance injected in the single injection through the needle.

11. The apparatus according to claim 1, wherein the apparatus comprises the substance, and wherein the substance comprises a depilatory agent.

12. The apparatus according to any one of claims 1-11, further comprising a cartridge, pre-filled with the substance, couplable to the housing, for providing the substance in a plurality of injections.

13. The apparatus according to claim 12, wherein the needle is couplable to the housing by being couplable to the cartridge, and wherein the needle and the cartridge are couplable to the housing by the user, prior to use of the apparatus.

14. The apparatus according to claim 12, wherein the cartridge is pre-filled with powder of botulinum toxin, and the injection driver is movable in a reverse direction to draw solution into the cartridge and facilitate suspension of the powder after receipt of the cartridge in the housing.

15. A substance-administration method, comprising:

selecting a single dosage of a substance by selecting one of a plurality of selectable dosages from a substance-administration apparatus comprising:

a housing, a needle couplable to the housing, a dosage regulator coupled to the housing which regulates the dosage of the substance from one of the plurality of selectable dosages including at least one dosage that is less than or equal to 10 ul, an electromechanical motor automatically actuated by the dosage regulator in a pulsatile manner, the motor being drivingly coupled to a rotator, which rotates about a central axis thereof, an injection driver for driving the substance through the needle, the injection driver having a rotatable gear system drivingly coupled to the rotator, wherein actuation of the motor in the pulsatile manner rotates the rotator and the coupled gear system in the pulsatile manner, to, in turn, drive the injection driver in the pulsatile manner to automatically produce a series of bursts of pressure in the housing that expel the single selected dosage of the substance through the needle at a controlled rate;

inserting the needle into skin of a subject to a depth of 0.3-2.5 mm, the needle having an outer diameter that is less than 0.23 mm;

expelling the single selected dosage of the substance through the needle at a controlled rate by automatically producing the series of bursts of pressure in the device; and administering the selected dosage of the substance through the needle.

16. The method according to claim 15, wherein inserting the needle comprises inserting the needle to a depth of 1-2.5 mm.

17. The method according to claim 15, wherein the plurality of selectable dosages further includes at least one dosage that is greater than 10 ul, and wherein selecting comprises selecting the at least one dosage that is greater than 10 ul.

18. The method according to claim 15, wherein the plurality of selectable dosages does not include any dosages that are greater than 50 ul, and wherein selecting comprises selecting a dosage from the plurality of selectable dosages that does not include any dosages that are greater than 50 ul.

19. The method according to claim 15, wherein the at least one dosage is 5-10 ul, and wherein selecting comprises selecting the at least one dosage that is 5-10 ul.

20. The method according to claim 15, wherein the at least one dosage is 1-5 ul, and wherein selecting comprises selecting the at least one dosage that is 1-5 ul.

21. The method according to claim 15, wherein the outer diameter of the needle is less than 0.21 mm, and wherein inserting the needle comprises inserting the needle that has an outer diameter that is less than 0.21 mm.

22. The method according to claim 15, wherein the substance includes a depilatory agent, and wherein administering the substance comprises administering the depilatory agent.

23. The method according to claim 15, wherein the substance includes a viscous substance, and wherein administering the substance comprises administering the viscous substance.

24. The method according to any one of claims 15-23, further comprising coupling to the needle a cartridge that is pre-filled with the substance, and providing the substance from the cartridge in a plurality of injections.

25. The method according to claim 24, wherein the cartridge is pre-filled with powder of botulinum toxin, and wherein the method further comprises suspending the powder prior to the providing the substance from the cartridge in the plurality of injections.

26. The method according to any one of claims 15-23, wherein inserting the needle in the skin comprises inserting the needle in at least one site selected from the group consisting of: skin of a face of the subject and skin of a neck of the subject.

27. The method according to claim 26, wherein inserting the needle in the at least one selected site comprises inserting the needle and administering the substance at at least 5 sites.

28. The method according to claim 26, wherein inserting the needle in the at least one selected site comprises inserting the needle at two sites separated by less than 1 mm.

* * * * *